United States Patent
Duque et al.

(10) Patent No.: US 10,441,376 B2
(45) Date of Patent: *Oct. 15, 2019

(54) ALTERNATE INSTRUMENT REMOVAL

(71) Applicant: Intuitive Surgical Operations, Inc., Sunnyvale, CA (US)

(72) Inventors: Grant Duque, San Jose, CA (US); Gregory W. Dachs, II, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 14/992,517

(22) Filed: Jan. 11, 2016

(65) Prior Publication Data
US 2016/0199139 A1  Jul. 14, 2016

Related U.S. Application Data

(63) Continuation of application No. 12/976,604, filed on Dec. 22, 2010, now Pat. No. 9,241,766.

(51) Int. Cl.
*A61B 90/11* (2016.01)
*A61B 34/30* (2016.01)
*A61B 17/00* (2006.01)

(52) U.S. Cl.
CPC .............. *A61B 90/11* (2016.02); *A61B 34/30* (2016.02); *A61B 2017/00477* (2013.01); *A61B 2560/0443* (2013.01)

(58) Field of Classification Search
CPC . A61B 34/30; A61B 2560/0443; A61B 50/00; A61B 46/00; A61B 2017/00477
See application file for complete search history.

(56) References Cited

U.S. PATENT DOCUMENTS

| | | |
|---|---|---|
| 5,201,742 A | 4/1993 | Hasson |
| 6,007,550 A | 12/1999 | Wang et al. |
| 6,279,413 B1 | 8/2001 | Terada et al. |
| 6,309,397 B1 | 10/2001 | Julian et al. |
| 6,620,173 B2 | 9/2003 | Gerbi et al. |
| 7,326,198 B2 | 2/2008 | Desarzens et al. |

(Continued)

OTHER PUBLICATIONS

Vertut, Jean and Phillipe Coiffet, Robot Technology: Teleoperation and Robotics Evolution and Development, English translation, Prentice-Hail, Inc., Inglewood Cliffs, NJ, USA 1986, vol. 3A, 332 pages.

*Primary Examiner* — Richard G Louis

(57) ABSTRACT

Minimally invasive robotic surgical instruments and related methods are disclosed. A surgical instrument includes an interface fitting that couples a proximal chassis of the instrument with a holding fixture of a robotic manipulator. A securing feature releasably prevents relative axial sliding between the interface fitting and the chassis. In response to binding of the surgical instrument within a minimally invasive surgical site so as to inhibit removal of the surgical instrument from the surgical site and inhibit disengagement of the interface fitting from the holding fixture, the securing feature can be released to allow relative axial sliding between the interface fitting and the chassis, thereby allowing the holding fixture and the interface fitting to be separated from the rest of the surgical instrument and repositioning of the robotic manipulator out of the way.

21 Claims, 9 Drawing Sheets

(56) References Cited

U.S. PATENT DOCUMENTS

| | | |
|---|---|---|
| 9,241,766 B2 | 1/2016 | Duque et al. |
| 2001/0034526 A1 | 10/2001 | Kuslich et al. |
| 2002/0120252 A1 | 8/2002 | Brock et al. |
| 2002/0169471 A1 | 11/2002 | Ferdinand |
| 2003/0216723 A1* | 11/2003 | Shinmura .............. A61B 90/25 606/34 |
| 2006/0074406 A1 | 4/2006 | Cooper et al. |
| 2006/0095022 A1 | 5/2006 | Moll et al. |
| 2006/0235436 A1 | 10/2006 | Anderson et al. |
| 2007/0016174 A1 | 1/2007 | Millman et al. |
| 2007/0142824 A1 | 6/2007 | Devengenzo et al. |
| 2007/0239206 A1 | 10/2007 | Shelton, IV et al. |
| 2008/0243106 A1 | 10/2008 | Coe et al. |
| 2008/0249551 A1 | 10/2008 | Sunaoshi et al. |
| 2009/0031842 A1 | 2/2009 | Kawai et al. |
| 2009/0264899 A1* | 10/2009 | Appenrodt ........... A61N 1/0529 606/130 |
| 2009/0287043 A1 | 11/2009 | Naito et al. |
| 2009/0292165 A1* | 11/2009 | Sugiyama .............. A61B 34/71 600/106 |
| 2010/0082040 A1 | 4/2010 | Sahni |
| 2010/0249817 A1 | 9/2010 | Mark |
| 2010/0286669 A1 | 11/2010 | Greer et al. |
| 2013/0110129 A1* | 5/2013 | Reid .................. A61B 19/2203 606/130 |

* cited by examiner

ALTERNATE INSTRUMENT REMOVAL

CROSS REFERENCE TO RELATED APPLICATIONS

The present application is a Continuation of U.S. Ser. No. 12/976,604 filed Dec. 22, 2010 (Allowed); the full disclosure which is incorporated herein by reference in its entirety for all purposes.

BACKGROUND

Minimally-invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally-invasive surgical techniques. Also, patient recovery times, patient discomfort, surgical side effects, and time away from work may also be reduced with minimally-invasive surgery.

A common form of minimally-invasive surgery is endoscopy, and a common form of endoscopy is laparoscopy, which is minimally-invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally-invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three-dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Non-robotic linear clamping, cutting, and stapling devices have been employed in many different surgical procedures. For example, such devices can be used in a lower anterior resection (LAR) to resect a cancerous or anomalous tissue from the proximal (upper) two-thirds of the rectum. In an LAR, however, it is not uncommon for the surgical instrument to be fully inserted (i.e., the instrument shaft becomes fully inserted) during the procedure. And in some instances, a high force clamping instrument such as a stapler device may become clamped on tissue and unable to unclamp. When both of these situations occur simultaneously (i.e., instrument fully inserted and the end effector device unable to unclamp), it may be necessary to decouple the surgical instrument from the robotic system to effectively deal with the situation. With existing instruments and robotic systems, however, it may be difficult if not impossible to decouple the surgical instrument from the robotic system in such a scenario.

BRIEF SUMMARY

Surgical instruments for use with a robotic manipulator of a minimally invasive surgical system and methods for using a surgical instrument with a robotic manipulator of a minimally invasive surgical system are disclosed. The disclosed surgical instruments and methods can, for example, ensure that a surgical instrument can be decoupled from a robotic manipulator when an end effector clamping device is unable to be unclamped from patient tissue while the surgical instrument is fully inserted into the patient. By decoupling the surgical instrument from the robotic manipulator, the robotic manipulator can be repositioned out of the way of efforts to deal with the bound surgical instrument.

Thus, in a first aspect, a method is provided for using a surgical instrument with a robotic manipulator of a minimally invasive surgical system. The method includes providing a surgical instrument that includes an elongate shaft extending along an axis between a distal end and a proximal end, a chassis disposed at the proximal end, and an end effector disposed at the distal end. The chassis includes a frame, an interface fitting demountably coupled with the frame via sliding engagement along the axis between the frame and the interface fitting, and a securing feature that is operable to prevent relative axial sliding between the interface fitting and the frame. The chassis is mounted onto a holding fixture of the robotic manipulator by engaging a mounting feature of the interface fitting with a complementary-shaped mounting feature of the holding fixture. And the end effector is articulated within a minimally invasive surgical site. In response to binding of the surgical instrument within the surgical site so as to inhibit removal of the end effector and shaft from the surgical site, and so as to inhibit disengagement of the mounting feature of the interface fitting from the mounting feature of the holding fixture, the securing feature is released so as to allow relative sliding between the interface fitting and the frame. The frame, shaft, and end effector of the surgical instrument are demounted from the interface fitting of the surgical instrument and the holding fixture of the robotic manipulator by moving the interface fitting relative to the frame along the axis.

The above method can include additional acts. For example, the method can include sliding the interface fitting into engagement with the frame. And the method can include securing the interface fitting in engagement with the frame via the securing feature.

In many embodiments, the securing feature includes a removable fastener. For example, the securing feature can include a plurality of removable fasteners.

In many embodiments, the interface fitting and the frame include complementary-shaped interfacing features. For example, the complementary interfacing features can include a slot extending along the axis. And the complementary-shaped interfacing features of the interface fitting and the frame can include two slots extending along the axis, with the slots disposed on opposite sides of the frame. For example, the frame can include the two slots and the interface fitting can include two protruding mounting features extending along the axis. And each of the protruding mounting features can include a flange extending along the axis.

In another aspect, a surgical instrument is provided for use with a robotic manipulator of a minimally invasive surgical system, the robotic manipulator having a holding fixture. The surgical instrument includes an elongate shaft extending along an axis between a distal end and a proximal end, a chassis disposed at the proximal end, and an end effector disposed at the distal end. The chassis includes a frame supporting the shaft, an interface fitting demountably coupled with the frame via sliding engagement along the axis between the frame and the interface fitting, and a securing feature releasably preventing relative axial sliding between the interface fitting and the frame. The interface fitting has a mounting feature receivable by the holding fixture of the robotic manipulator so as to mount the instrument thereon. The end effector is articulatable relative to the shaft so as to manipulate tissue within a minimally invasive surgical site. The securing feature is configured for releasing in response to binding of the surgical instrument within the surgical site, the binding inhibiting removal of the end effector and shaft from the surgical site and disengagement of the mounting feature of the interface fitting from the holding fixture. Releasing the securing features allows relative sliding between the interface fitting and the frame so as to promote demounting of the frame, shaft, and end effector of the surgical instrument from the interface fitting of the surgical instrument and the holding fixture of the robotic manipulator by moving the interface fitting relative to the frame along the axis.

In many embodiments, the securing feature includes a removable fastener. For example, the securing feature can include a plurality of removable fasteners.

In many embodiments, the interface fitting and the frame include complementary-shaped interfacing features. For example, the complementary interfacing features can include a slot extending along the axis. And the complementary-shaped interfacing features of the interface fitting and the frame can include two slots extending along the axis, with the slots disposed on opposite sides of the frame. For example, the frame can include the two slots and the interface fitting can include two protruding mounting features extending along the axis. And each of the protruding mounting features can include a flange extending along the axis.

The interface fitting can have a u-shaped configuration that interfaces with the frame on three sides of the frame. And the u-shaped interface fitting can be received within two slots in the frame disposed on opposite sides of the frame. The securing feature can include two removable fasteners, each of the removable fasteners coupling with a nut retained by the frame.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention can be practiced without the specific details. Furthermore, well-known features may be omitted or simplified in order not to obscure the embodiment being described.

Minimally-Invasive Robotic Surgery

Figure 1:
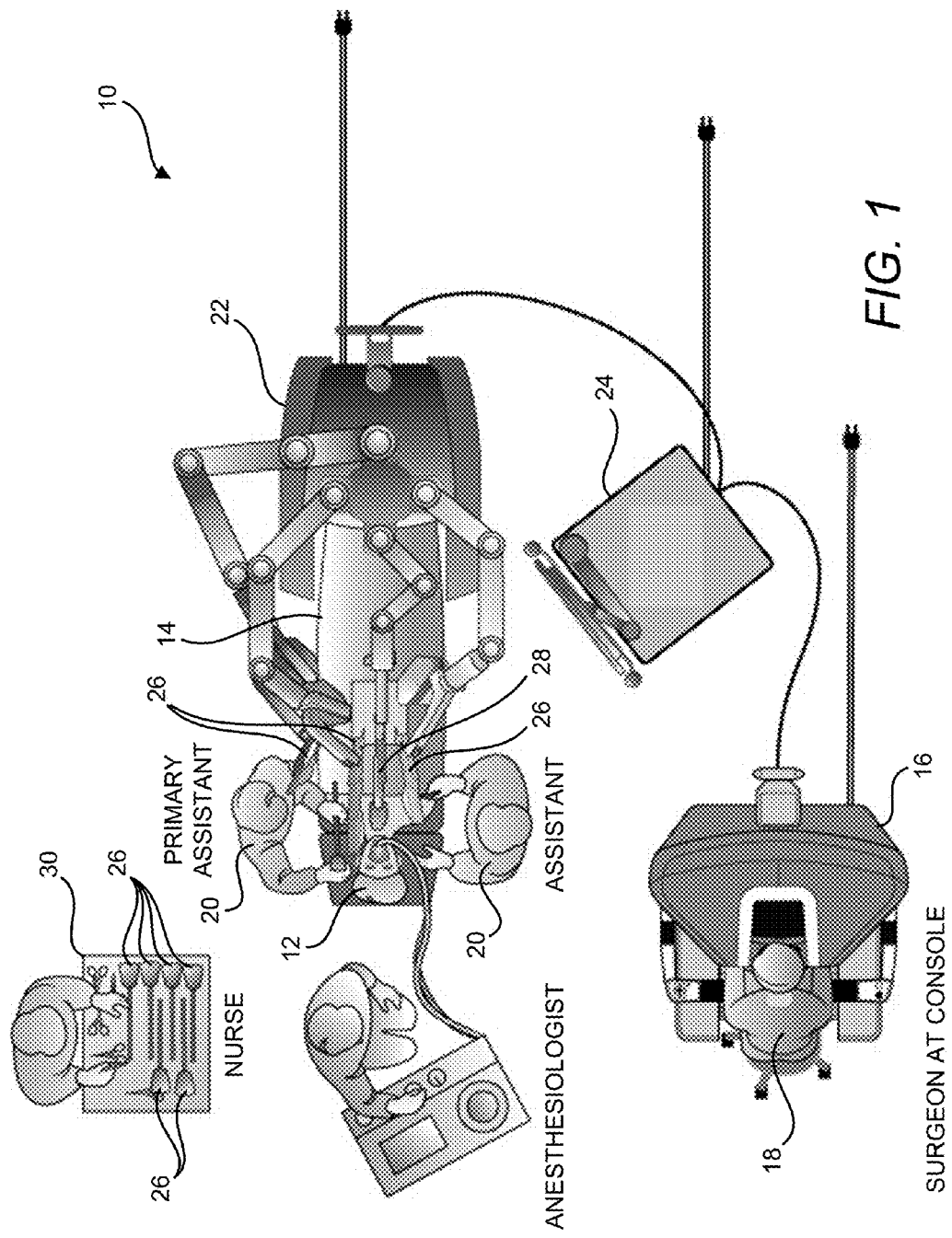
FIG. 1 is a plan view of a minimally-invasive robotic surgery system being used to perform a surgery, in accordance with many embodiments.

Referring now to the drawings, in which like reference numerals represent like parts throughout the several views, FIG. 1 is a plan view illustration of a Minimally-Invasive Robotic Surgical (MIRS) system 10, typically used for performing a minimally-invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient-Side Cart 22 (surgical robot), and an Electronics Cart 24. The Patient Side Cart 22 can manipulate at least one removably coupled tool assembly 26 (hereinafter simply referred to as a "tool") through a minimally-invasive incision in the body of the Patient 12 while the Surgeon 18 views the surgical site through the Console 16. An image of the surgical site can be obtained by an endoscope 28, such as a stereoscopic endoscope, which can be manipulated by the Patient-Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient-Side Cart 22, and replace it with another tool 26 from a tray 30 in the operating room.

Figure 2:
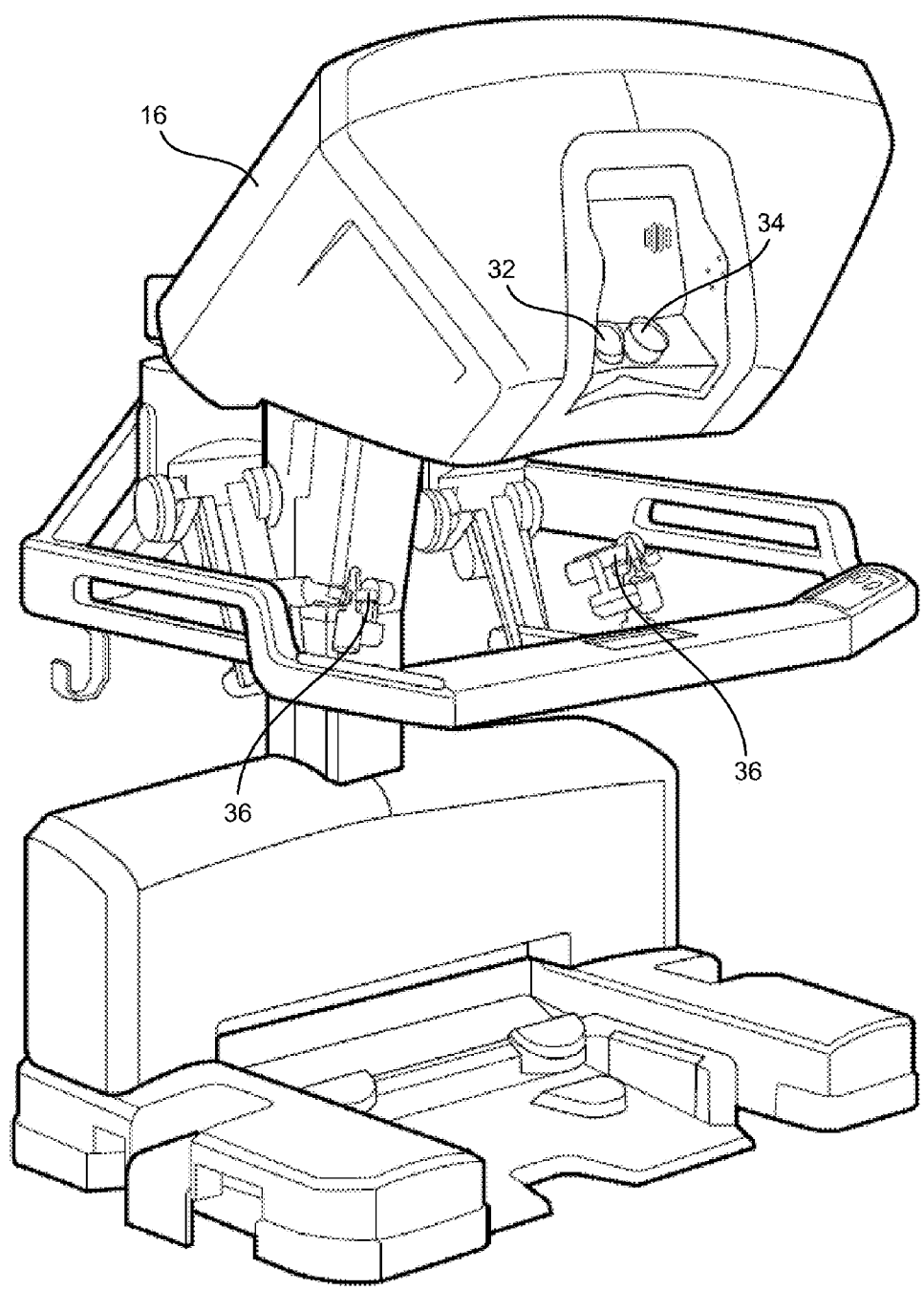
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient-Side Cart 22 (shown in FIG. 1) to manipulate one or more tools. The input control devices 36 can provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) can be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
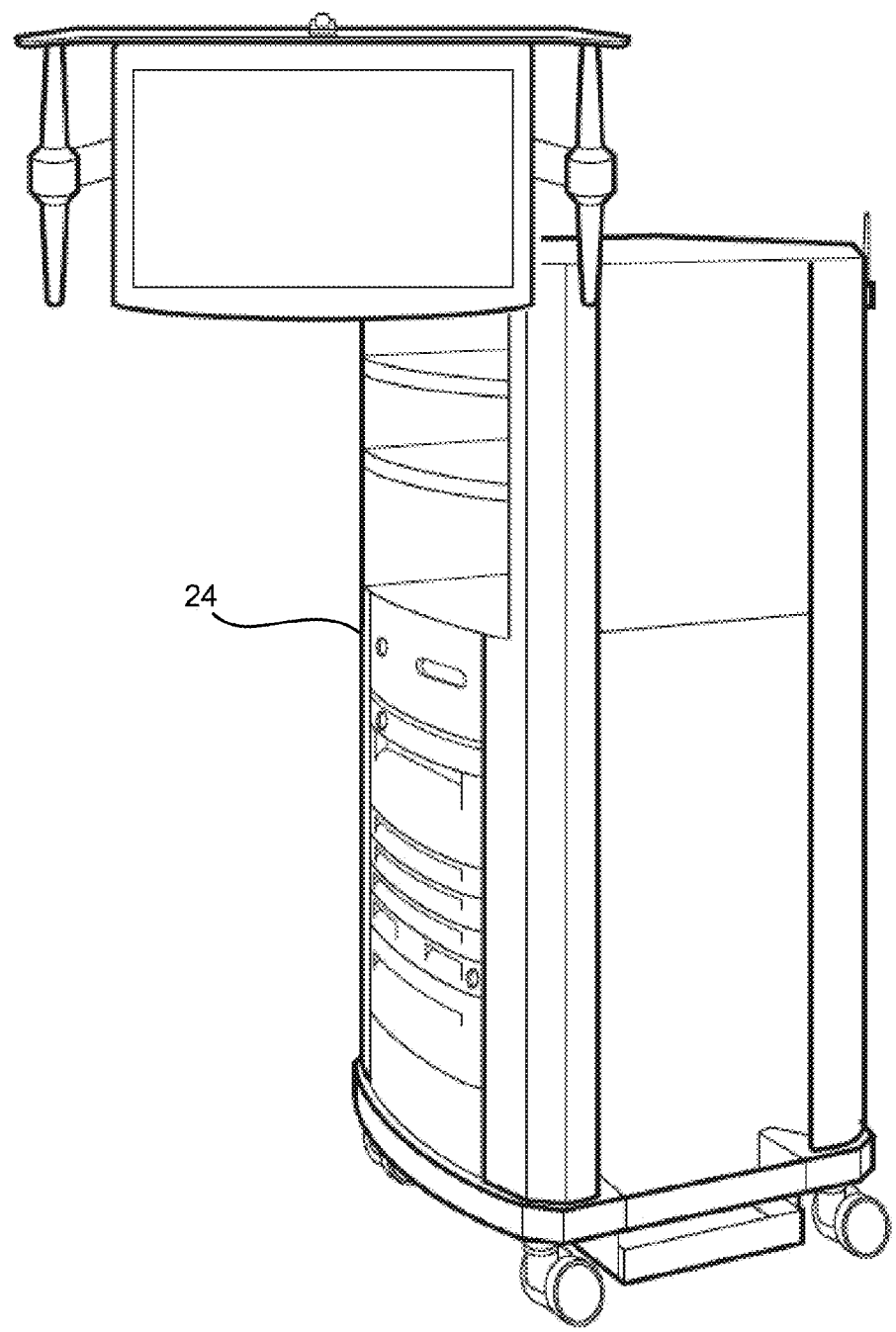
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on any other suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image-capture device, such as optical aberrations.

Figure 4:
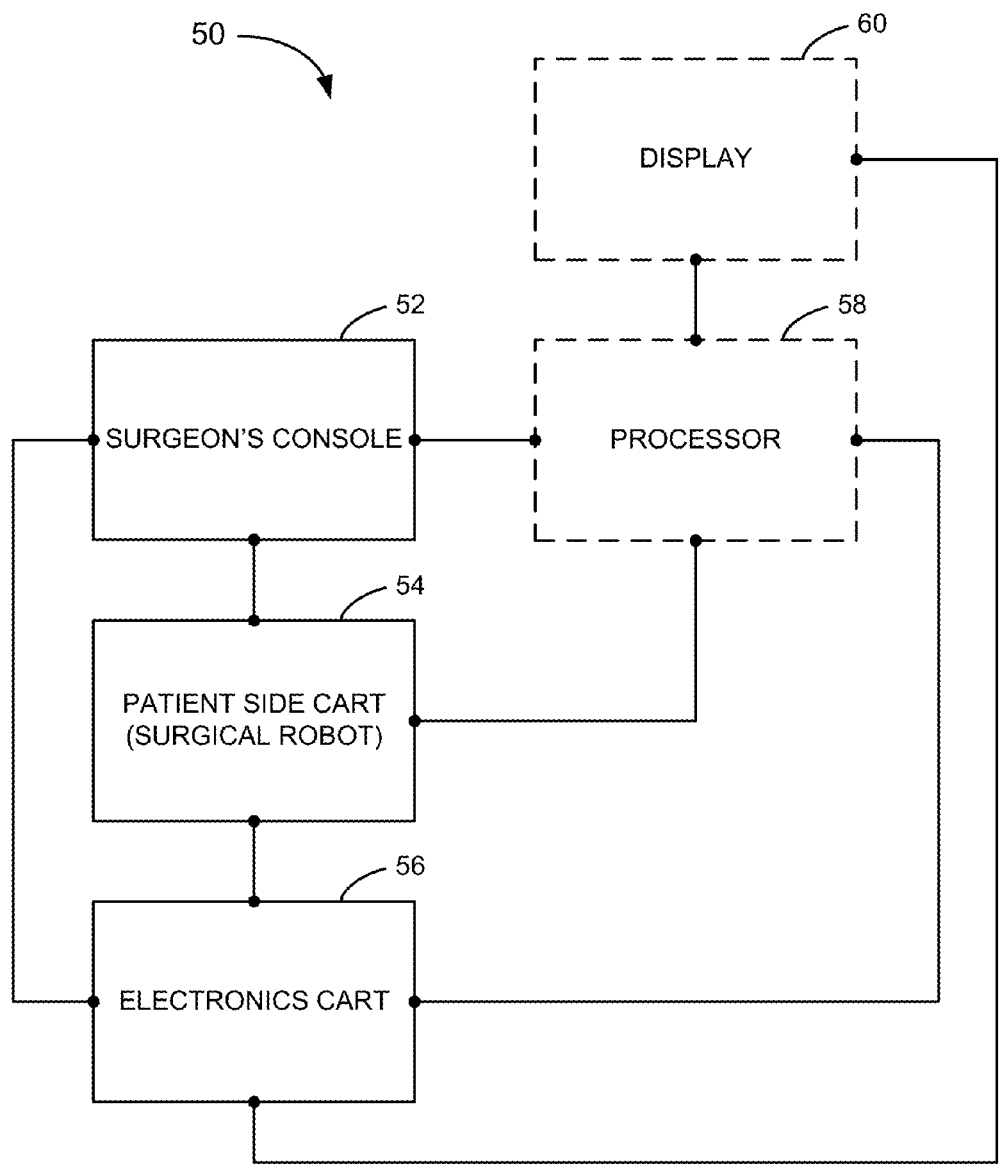
FIG. 4 is a simplified diagrammatic illustration of a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient-Side Cart (Surgical Robot) 54 (such as Patent-Side Cart 22 in FIG. 1) during a minimally-invasive procedure. The Patient-Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient-Side Cart 54 can output the captured images for processing outside the Electronics Cart 56. For example, the Patient-Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or any other related images.

Figure 5B:
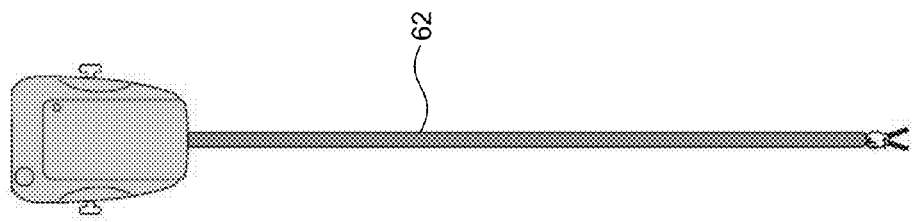
FIG. 5B is a front view of a robotic surgical tool.
Figure 5A:
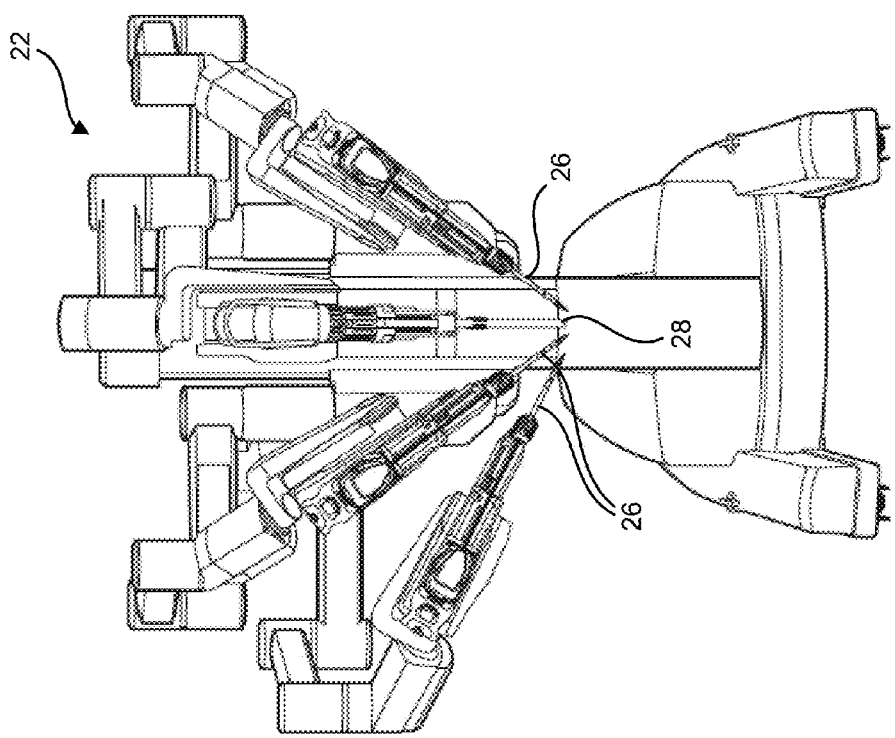
FIG. 5A is a front view of a patient-side cart (surgical robot) of a robotic surgery system, in accordance with many embodiments.

FIGS. 5A and 5B show a Patient-Side Cart 22 and a surgical tool 62, respectively. The surgical tool 62 is an example of the surgical tools 26. The Patient-Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Mounting and Demounting of a Bound Surgical Tool

Figure 6:
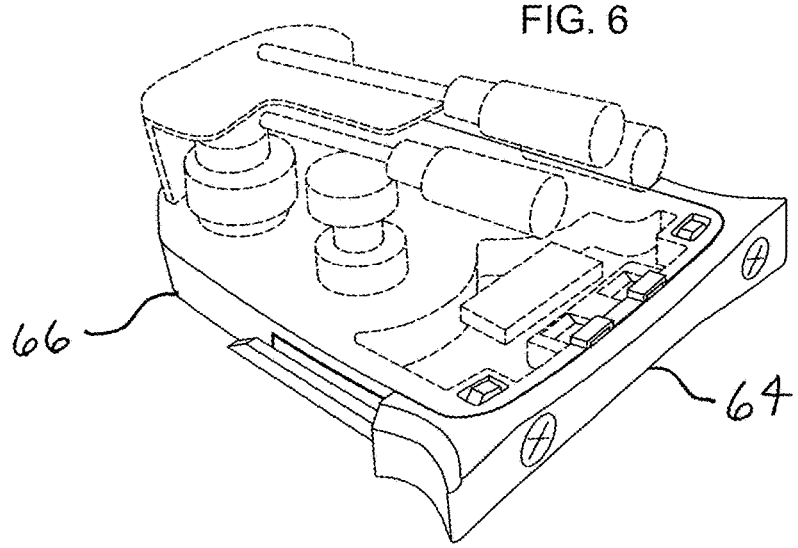
FIG. 6 is a perspective view of an interface fitting coupled with a frame of a proximal chassis of a robotic surgical tool, in accordance with many embodiments.
Figure 7:
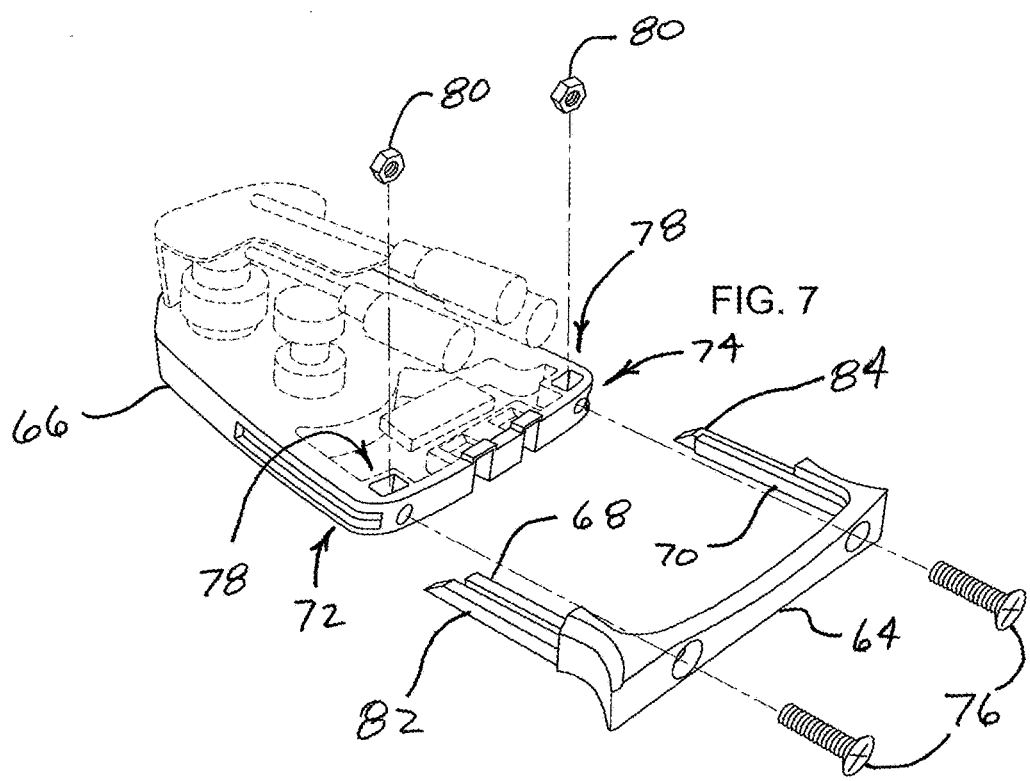
FIG. 7 is an exploded perspective view of components of FIG. 6.

FIGS. 6 and 7 illustrate the coupling of an interface fitting 64 coupled and a frame 66 of a proximal chassis of a robotic surgical tool for a minimally invasive robotic surgery system, in accordance with many embodiments. The interface fitting 64 has a u-shaped configuration that interfaces with the frame 66 on three sides of the frame. The interface fitting 64 includes first and second elongate flanges 68, 70 disposed on opposite sides of the interface fitting. The first and second elongate flanges 68, 70 are received within complementary shaped slots 72, 74, respectively, disposed on corresponding opposite sides of the frame. The interface fitting is coupled with the frame by sliding the first and second elongate flanges 68, 70 into the corresponding slots 72, 74 and installing two removable fasteners 76 to secure the interface fitting to the frame, thereby preventing relative axial sliding between the interface fitting and the frame. The frame includes two receptacles 78 configured to receive and rotationally restrain two nuts 80 for the two removable fasteners 76.

The interface fitting 64 provides mounting features that are receivable by a holding fixture of a robotic manipulator of a minimally invasive surgical system. The mounting features include two external flanges 82, 84 disposed on opposite sides of the interface fitting and configured to be received by respective complementary-shaped slots in the holding fixture of the robotic manipulator.

Figure 8:
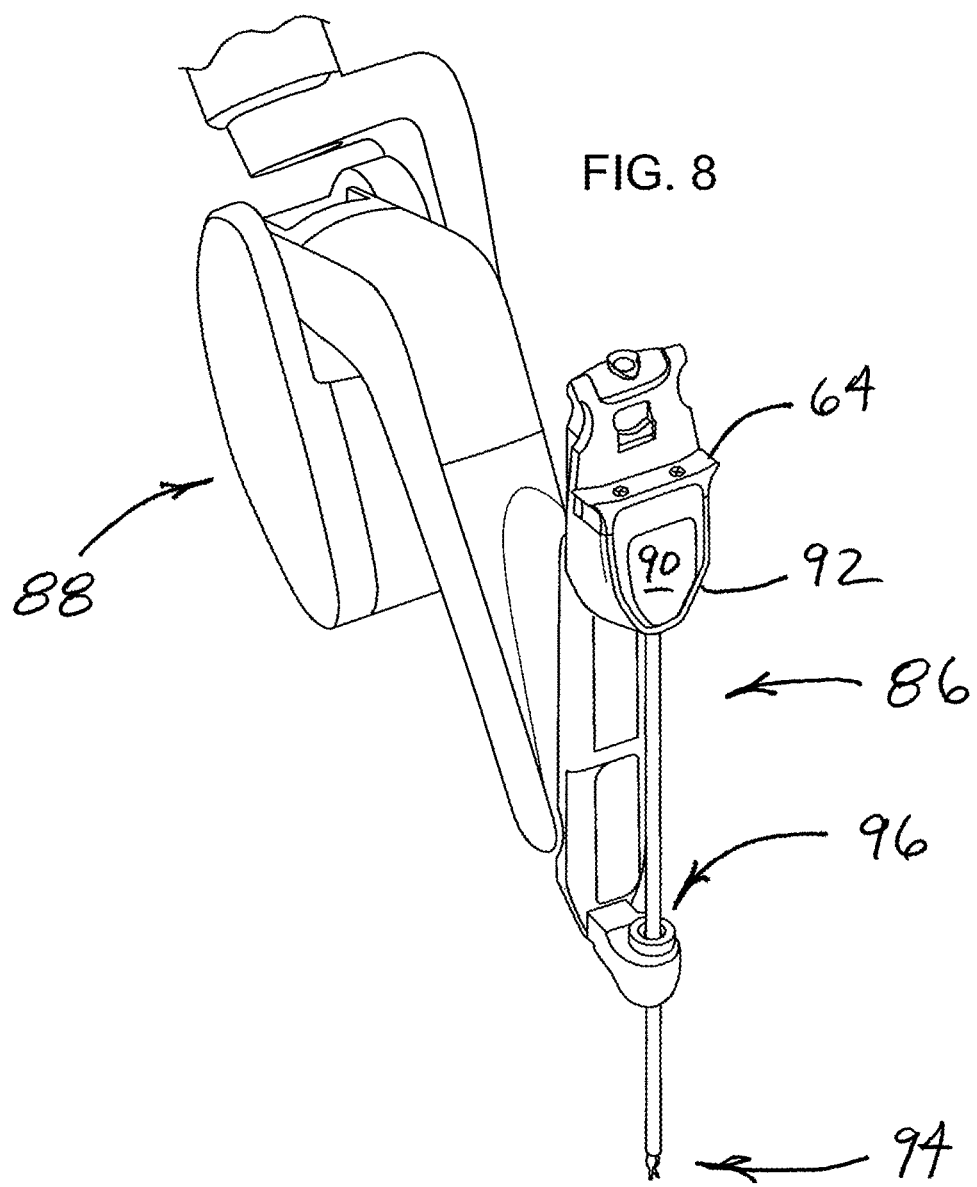
FIG. 8 is a perspective view of a robotic surgical tool and interface fitting assembly coupled to a robotic manipulator of a minimally invasive surgical system, in accordance with many embodiments.
Figure 9:
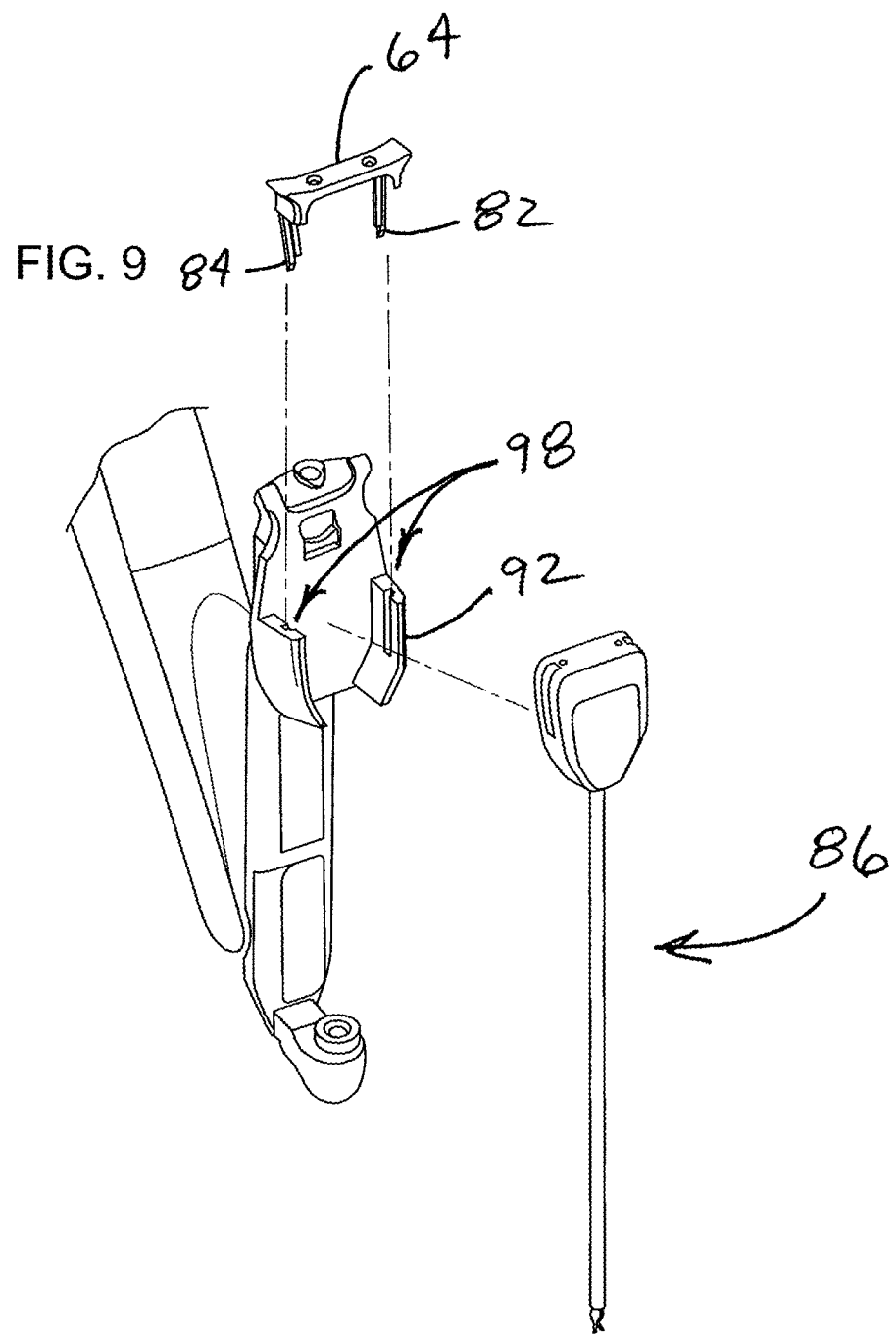
FIG. 9 is an exploded perspective view of components of FIG. 8 and illustrates decoupling of the robotic surgical tool from the robotic manipulator via the removal of the interface fitting, in accordance with many embodiments.

FIGS. 8 and 9 illustrate mounting and demounting of a surgical tool 86 to and from, respectively, a robotic manipulator 88 of a minimally invasive surgical system, in accordance with many embodiments. In FIG. 8, the interface fitting 64 is shown coupled with the frame of the proximal chassis 90, and the combined assembly is mounted to a holding fixture 92 of the robotic manipulator 88. In normal circumstances, the interface fitting can be coupled to the frame and the combined assembly can then be mounted to the holding fixture by inserting a distal end 94 of the surgical tool through a guide aperture 96 of the robotic manipulator 88 and mounting the combined assembly onto the holding fixture via relative sliding between the combined assembly and the holding fixture along a direction corresponding to receiving slots 98 in the holding fixture and the two external flanges 82, 84 of the interface fitting. Likewise, in regular circumstances, the combined assembly can be demounted from the holding fixture via a reverse relative sliding between the combined assembly and the holding fixture. A securing feature (not shown) can be used to selectively prevent relative sliding between the mounted combined assembly and the holding fixture so that the combined assembly is fully secured to the holding fixture 92.

FIG. 9 illustrates demounting the surgical tool from the robotic manipulator in response to binding of the surgical tool 86 within a surgical site so as to inhibit the removal of the surgical tool from the surgical site and disengagement of the combined assembly from the holding fixture of the robotic manipulator. By removing the two removable fasteners 76 (shown in FIGS. 6 and 7), the interface fitting can be decoupled from engagement with both the frame 66 and the holding fixture 92, thereby decoupling the frame 66 from the holding fixture 92. The robotic manipulator 88 can then be moved out of the way, thereby providing increased access to the bound surgical instrument. Accordingly, a surgical instrument can be decoupled from a robotic manipulator when an end effector clamping device is unable to be unclamped from patient tissue while the surgical instrument is fully inserted into the patient. Likewise, this demounting process can be reversed to mount a surgical instrument to the robotic manipulator.

Figure 10:
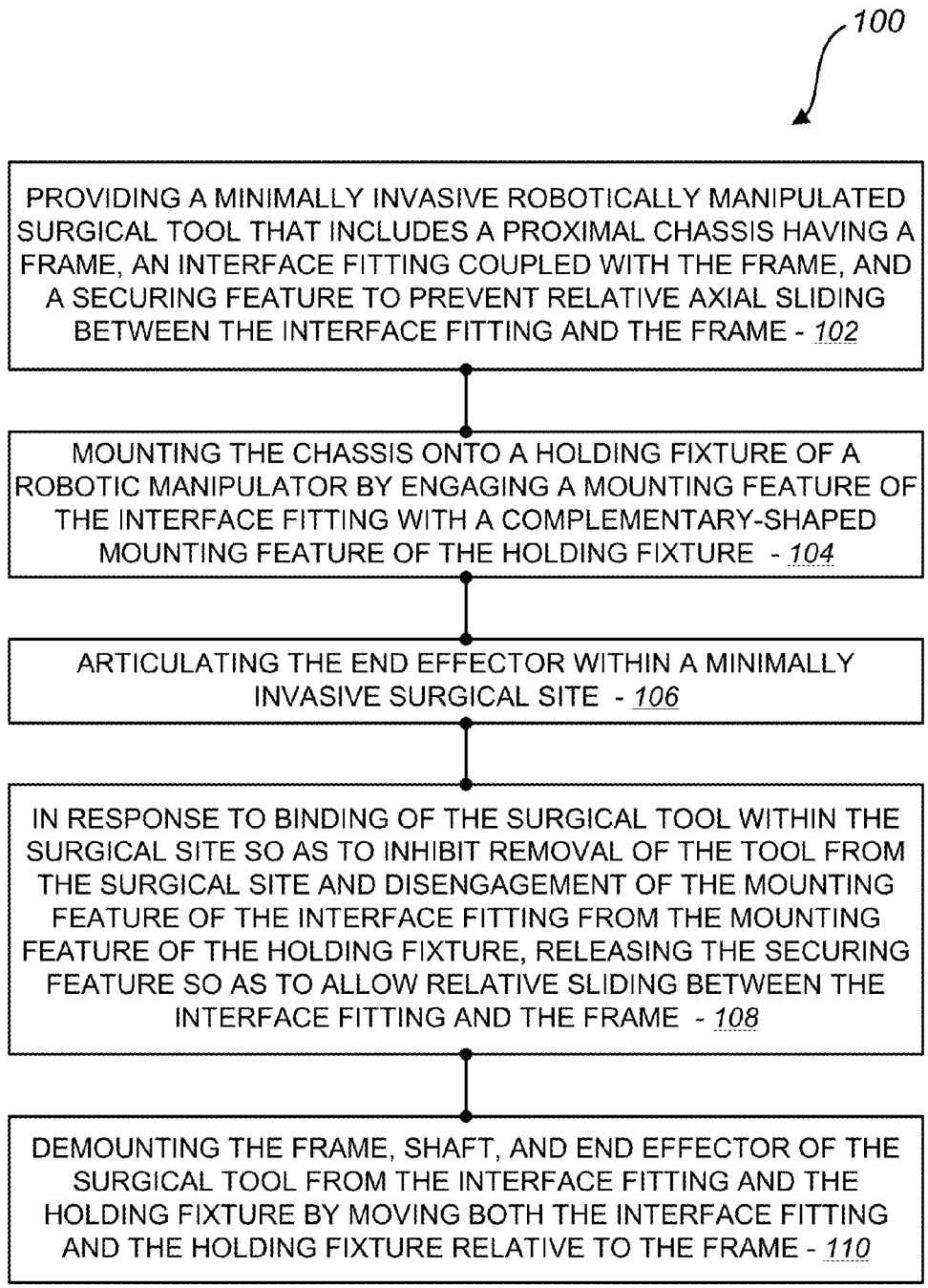
FIG. 10 is a simplified block diagram of a method for using a robotic surgical tool with a robotic manipulator of a minimally invasive surgical system, in accordance with many embodiments.

FIG. 10 illustrates a method 100 for using a surgical instrument with a robotic manipulator of a minimally surgical system, in accordance with many embodiments. The surgical tools and interface fittings disclosed herein can be used to practice the method 100.

In act 102, a surgical tool is provided that includes a proximal chassis having a frame, an interface fitting coupled with the frame, and a securing feature to prevent relative movement between the interface fitting and the frame. For example, the surgical tool can include an elongate shaft extending along an axis between a distal end and a proximal end, the proximal chassis, and an end effector disposed at the distal end. The interface fitting can be demountably coupled with the frame via sliding engagement along the axis between the frame and the interface fitting. The sliding engagement can be provided via complementary-shaped interfacing features on the interface fitting and the frame, such as a slot extending along the axis. For example, the complementary-shaped interfacing features of the frame can include two slots extending along the axis that are disposed on opposite sides of the frame. The complementary-shaped interfacing features of the interface fitting can include two protruding features, such as flanges, extending along the axis. And the securing feature can be operable to prevent relative axial sliding between the interface fitting and the frame. The securing feature can include one or more removable fasteners.

In act 104, the chassis is mounted onto a holding fixture of the robotic manipulator. For example, a mounting feature of the interface fitting can be engaged with a complementary-shaped mounting feature of the holding feature.

In act 106, the end effector is manipulated within a minimally invasive surgical site. For example, the end effector can be a cutting and stapling device that is used to resect a cancerous tissue.

In act 108, in response to binding of the surgical tool within the surgical site, the securing feature is released so as to allow relative sliding between the interface fitting and the frame. Such binding may inhibit removal of the end effector and shaft from the surgical site and inhibit disengagement of the mounting feature of the interface fitting from the mounting feature of the holding fixture.

In act 110, the frame, shaft, and end effector of the surgical tool is demounted from the interface fitting of the surgical tool and the holding fixture of the robotic manipulator by moving both the interface fitting and the holding fixture relative to the frame along the axis.

The method 100 can include additional acts. For example, the method can further include sliding the interface fitting into engagement with the frame. And the method 100 can further include securing the interface fitting in engagement with the frame via the securing feature.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical instrument for use with a surgical system manipulator having a holding fixture, the surgical instrument comprising:
   a chassis;
   an end effector coupled with the chassis, the end effector comprising a clamping mechanism that is manipulated via the surgical system manipulator;
   an interface fitting that is mountable to the chassis; and
   a securing feature;
   the chassis and the interface fitting coupled together being a combined assembly;
   the combined assembly being mountable to the holding fixture via movement of the combined assembly relative to the holding fixture in a mounting direction to produce a mounted configuration in which the combined assembly is held by the holding fixture and the chassis is in a mounted position and orientation relative to the holding fixture;
   the interface fitting being demountable from both the chassis and the holding fixture, while the chassis is in the mounted position and orientation relative to the holding fixture, to produce a demountable configuration in which the chassis is demountable from the holding fixture via movement of the chassis relative to the holding fixture in a demounting direction transverse to the mounting direction;
   the interface fitting constraining the combined assembly in the mounted configuration from moving in the demounting direction relative to the holding fixture; and
   the securing feature operable to secure the interface fitting to the chassis in the combined assembly and to release the interface fitting from the chassis to accommodate demounting of the interface fitting from both the chassis and the holding fixture.

2. The surgical instrument of claim 1, wherein the securing feature comprises a removable fastener.

3. The surgical instrument of claim 2, wherein the securing feature comprises a plurality of removable fasteners.

4. The surgical instrument of claim 1, wherein the chassis and the interface fitting together comprise a slot by which the interface fitting is mountable to the chassis.

5. The surgical instrument of claim 4, wherein the chassis and the interface fitting together comprise two slots by which the interface fitting is mountable to the chassis, one of the two slots being disposed on an opposite side of the chassis relative to the other of the two slots.

6. The surgical instrument of claim 5, wherein the chassis and the interface fitting together comprise two protruding mounting features, each of the two protruding mounting features being shaped to be accommodated via a respective one of the two slots.

7. The surgical instrument of claim 1, wherein the interface fitting interfaces with the chassis on three sides of the chassis.

8. The surgical instrument of claim 1, wherein the securing feature comprises two removable fasteners, each of the removable fasteners coupling with a nut retained by the chassis.

9. A method of mounting a surgical instrument to a surgical system manipulator and demounting the surgical instrument from the surgical system manipulator, the surgical instrument including an end effector, the manipulator having a holding fixture, the method comprising:
   mounting a surgical instrument assembly to the holding fixture by moving the surgical instrument assembly relative to the holding fixture in a mounting direction to produce a mounted configuration in which the surgical instrument assembly is held by the holding fixture; the surgical instrument assembly including the surgical instrument, an interface fitting mounted to a chassis of the surgical instrument, and a securing feature that secures the interface fitting to the chassis;
   in response to binding of the surgical instrument within a surgical site so as to inhibit removal of the end effector from the surgical site:
      operating the securing feature to accommodate demounting of the interface fitting from the chassis;
      demounting the interface fitting from the chassis to produce a demountable configuration in which the chassis is demountable from the holding fixture via movement of the chassis relative to the holding fixture in a demounting direction transverse to the mounting direction; and
      demounting the chassis from the holding fixture by moving the chassis in the demounting direction relative to the holding fixture.

10. The method of claim 9, wherein demounting the interface fitting from the chassis comprises sliding the interface fitting relative to the chassis.

11. The method of claim 10, wherein sliding the interface fitting relative to the chassis comprises sliding a protruding feature out of engagement with a slot.

12. The method of claim 10, wherein sliding the interface fitting relative to the chassis comprises sliding each of two protruding features out of engagement with a respective slot.

13. The method of claim 9, wherein operating the securing feature comprises removing a fastener.

14. The method of claim 13, wherein removing the fastener comprises rotating the fastener to disengage the fastener from a nut retained by the chassis.

15. The method of claim 13, wherein operating the securing feature comprises removing a plurality of fasteners.

16. The method of claim 9, further comprising articulating the end effector within the surgical site.

17. A surgical system, comprising:
   a surgical system manipulator comprising a holding fixture; and
   a surgical instrument comprising:
      a chassis;
      an end effector coupled with the chassis;
      an interface fitting removably mounted to the chassis; and
      a securing feature;
      the chassis and the interface fitting coupled together being a combined assembly;
      the combined assembly being mountable to the holding fixture via movement of the combined assembly relative to the holding fixture in a mounting direction to produce a mounted configuration in which the combined assembly is held by the holding fixture and in which the chassis is in a mounted position and orientation relative to the holding fixture;
      the interface fitting being demountable from both the chassis and the holding fixture, while the chassis is in the mounted position and orientation relative to the holding fixture, to produce a demountable configuration in which the chassis is demountable from the holding fixture via movement of the chassis relative to the holding fixture in a demounting direction transverse to the mounting direction;

the interface fitting constraining the combined assembly in the mounted configuration from moving in the demounting direction relative to the holding fixture; and the securing feature configured to be operable to secure the interface fitting to the chassis in the combined assembly and to release the interface fitting from the chassis to accommodate demounting of the interface fitting from both the chassis and the holding fixture.

18. The surgical system of claim 17, wherein the chassis and the interface fitting together comprise two slots by which the interface fitting is mountable to the chassis, one of the two slots being disposed on an opposite side of the chassis relative to the other of the two slots.

19. The surgical system of claim 18, wherein the chassis and the interface fitting together comprise two protruding mounting features, each of the two protruding mounting features being shaped to be accommodated via a respective one of the two slots.

20. The surgical system of claim 17, wherein the interface fitting interfaces with the chassis on three sides of the chassis.

21. A surgical instrument, comprising:
a chassis;
an end effector coupled with the chassis;
a securing feature; and
an interface fitting;
wherein the chassis and the interface fitting are removably secured to each other by the securing feature; and
wherein the surgical instrument is configurable to:
 a mounting configuration of the surgical instrument to a holding fixture of a surgical system manipulator, in which the chassis and the interface fitting are secured to each other by the securing feature and are mountable to the holding fixture by sliding the chassis and the interface fitting in a mounting direction relative to the holding fixture;
 a first dismounting configuration of the surgical instrument from the holding fixture of the surgical system manipulator, in which the chassis and the interface fitting are secured to each other by the securing feature and are demountable from the holding fixture by sliding the chassis and the interface fitting in a direction opposite to the mounting direction relative to the holding fixture; and
 a second dismounting configuration of the surgical instrument from the holding fixture of the surgical system manipulator, in which the chassis and the interface fitting are not secured to each other by the securing feature, the interface fitting is demountable from both the chassis and the holding fixture by sliding the interface fitting in the direction opposite to the mounting direction relative to the holding fixture, and with the interface fitting demounted from both the chassis and the holding fixture, the chassis is demountable from the holding fixture by moving the chassis in a direction transverse to the mounting direction relative to the holding fixture.

\* \* \* \* \*